(12) United States Patent
Probst

(10) Patent No.: US 11,083,506 B1
(45) Date of Patent: Aug. 10, 2021

(54) MODULAR CRIMPABLE PLATE

(71) Applicant: DEPUY SYNTHES PRODUCTS, INC., Raynham, MA (US)

(72) Inventor: Troy Probst, Wilmington, DE (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 68 days.

(21) Appl. No.: 16/785,963

(22) Filed: Feb. 10, 2020

(51) Int. Cl.
*A61B 17/80* (2006.01)

(52) U.S. Cl.
CPC ................. *A61B 17/8023* (2013.01)

(58) Field of Classification Search
CPC . A61B 17/80; A61B 17/8004; A61B 17/8014; A61B 17/8023; A61B 17/8047; A61B 17/82; A61B 17/84; A61B 17/86; A61B 17/70; A61B 17/7001; A61B 17/7002; A61B 17/7004; A61B 17/7005; A61B 17/7007; A61B 17/7008; A61B 17/7019; A61B 17/701; A61B 17/7011; A61B 17/702; A61B 17/7022; A61B 17/7025; A61B 17/7047; A61B 17/7049; A61B 17/705
USPC ...................... 606/246–279, 280–299, 70, 71
See application file for complete search history.

(56) References Cited

U.S. PATENT DOCUMENTS

| | | | |
|---|---|---|---|
| 2,443,363 A | 4/1942 | Townsend et al. | |
| 2,406,832 A | 3/1945 | Hardinge | |
| 4,719,905 A * | 1/1988 | Steffee | A61B 17/7005 606/261 |
| 4,920,959 A | 5/1990 | Witzel et al. | |
| 5,330,473 A * | 7/1994 | Howland | A61B 17/7049 403/396 |
| 5,527,310 A | 6/1996 | Cole et al. | |
| 5,975,904 A | 11/1999 | Spiegel | |
| 6,136,002 A | 10/2000 | Shih et al. | |
| 6,616,669 B2 | 9/2003 | Ogilvie et al. | |
| 6,645,207 B2 | 11/2003 | Dixon et al. | |
| 6,706,044 B2 | 3/2004 | Kuslich et al. | |
| 7,344,537 B1 | 3/2008 | Mueller et al. | |
| 8,114,080 B2 | 2/2012 | Schulze | |
| 10,166,054 B2 | 1/2019 | Woodburn et al. | |
| 10,188,439 B2 | 1/2019 | Woodburn et al. | |
| 10,258,402 B2 | 4/2019 | Silva et al. | |
| 10,478,237 B2 | 11/2019 | Silva et al. | |
| 2002/0169449 A1 | 11/2002 | Kuslich et al. | |
| 2004/0039388 A1 | 2/2004 | Biedermann et al. | |

(Continued)

OTHER PUBLICATIONS

Depuye Synthes Vet, "Technical Guide: Clam and Rod Internal Fixation (CRIF) System", Modular implant system or orthopaedic conditions: Surgical Technique, 24 pages. (2013).

*Primary Examiner* — Si Ming Ku
(74) *Attorney, Agent, or Firm* — Kramer Amado PC

(57) ABSTRACT

A modular crimpable bone plate system, including: a first rod and a second rod; and a plurality of rod connectors, wherein the rod connectors further include: a first tube and a second tube configured to slide over the first and second rods; a first leg and a second leg each connected between the first and second tubes; and an opening between the first and second legs and between the first and second tubes, where in the opening is configured to accept a screw head of a screw; wherein the first and second tubes are configured to be crimped onto the first and second rods, and wherein the first leg and second leg are configured to be crimped onto the screw.

20 Claims, 6 Drawing Sheets

(56) References Cited

U.S. PATENT DOCUMENTS

| | | |
|---|---|---|
| 2005/0277923 A1 | 12/2005 | Sweeney |
| 2006/0064092 A1* | 3/2006 | Howland ........... A61B 17/7007 606/261 |
| 2006/0079892 A1 | 4/2006 | Roychowdhury et al. |
| 2008/0147124 A1 | 6/2008 | Haidukewych et al. |
| 2009/0024171 A1 | 1/2009 | Leone |
| 2018/0049786 A1 | 2/2018 | Brace et al. |
| 2019/0117284 A1 | 4/2019 | Woodburn et al. |

* cited by examiner

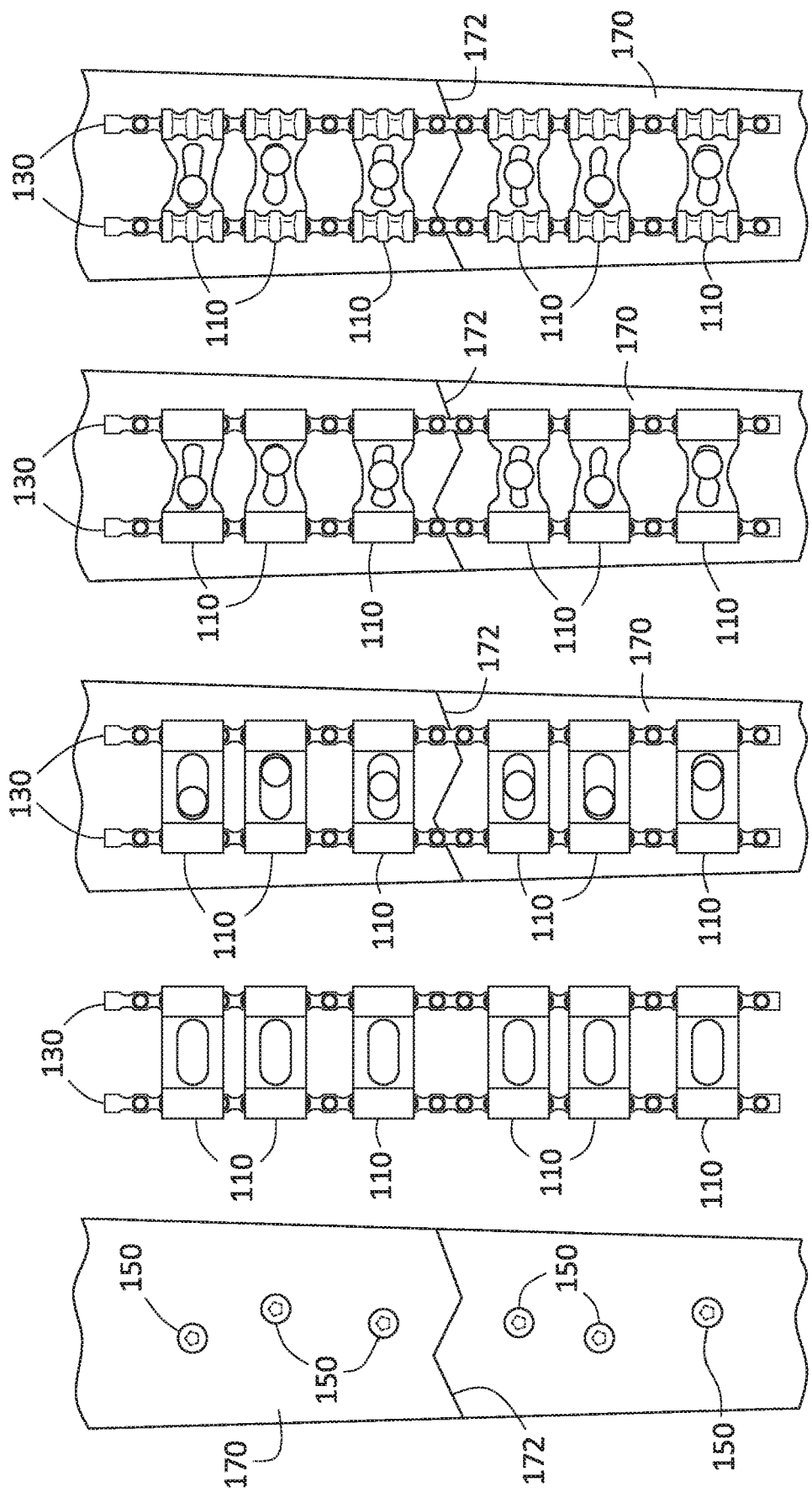

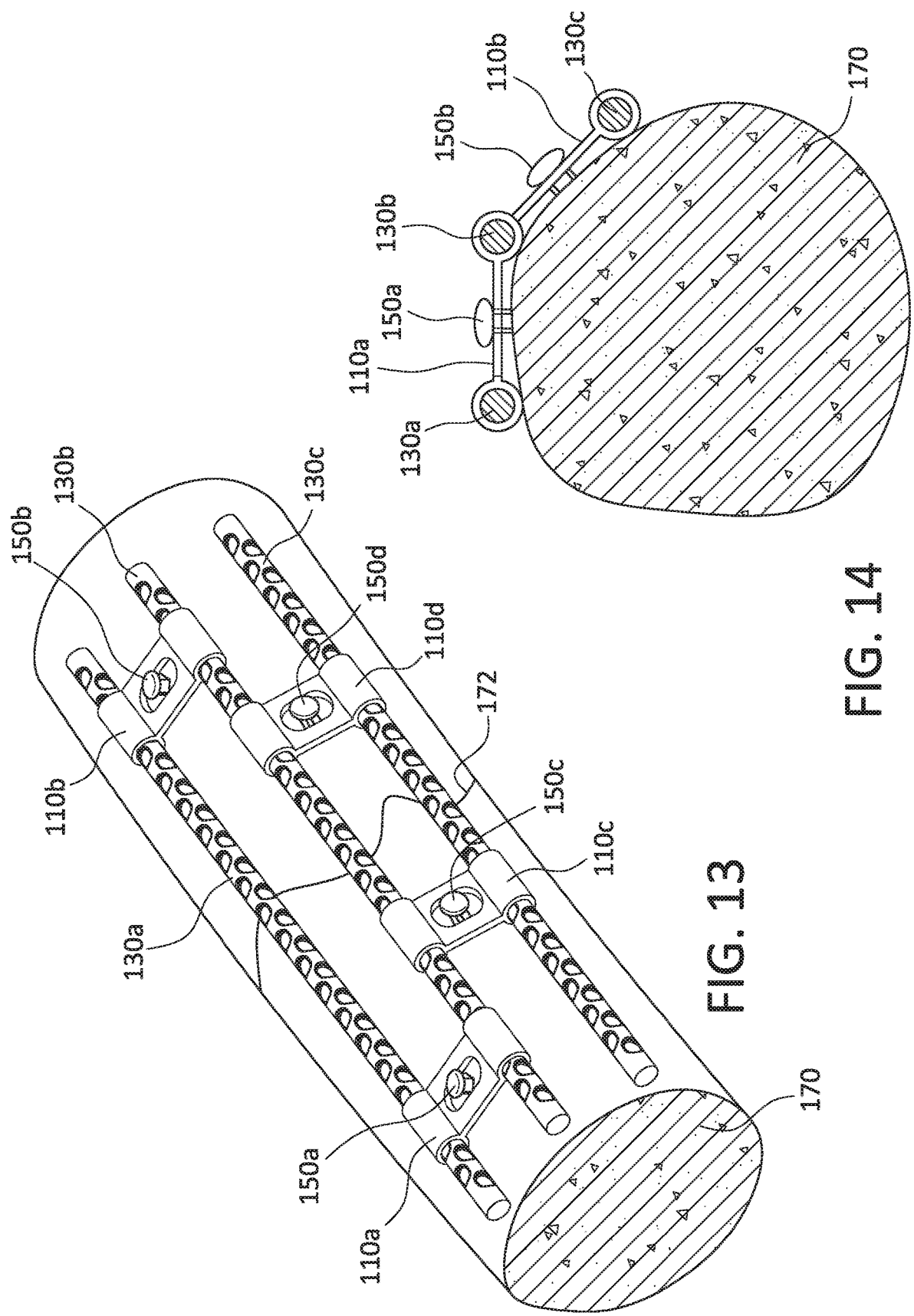

MODULAR CRIMPABLE PLATE

TECHNICAL FIELD

Various exemplary embodiments disclosed herein relate generally to a modular crimpable plate for use in the internal fixation of bones.

BACKGROUND

In various orthopedic surgical procedures, it is often necessary to secure or stabilize two or more portions of bone or soft tissue relative to one another. This need is often the result of a bone or soft tissue injury, such as an acute fracture of the bone. To ensure that the damaged bone fragments are capable of properly regenerating, it is important that the bone fragments be adequately stabilized during the regeneration process. To adequately stabilize the injured bone fragments and/or soft tissue, a bone plate may be installed on the fractured bone.

Bone plates are used for internal fixation of fractures. The plate is fixed to the bone by application of screws on both sides of the fracture. Bone plates are now widely accepted with different standard techniques of osteosynthesis, throughout the skeleton. Different anatomical locations demand different shapes and sizes of plates. For a plate to be effective means of fixation it should meet the following requirements: it should be of appropriate width and thickness for the given bone; the plate must have adequate hold on either side of the fracture; the plate must be closely opposed to the contour of bone; and the plate must neutralize all forces acting on the fracture, i.e., bending, compression, shear and torque

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a modular crimpable bone plate system, including: a first rod and a second rod; and a plurality of rod connectors, wherein the rod connectors further include: a first tube and a second tube configured to slide over the first and second rods; a first leg and a second leg each connected between the first and second tubes; and an opening between the first and second legs and between the first and second tubes, where in the opening is configured to accept a screw head of a screw; wherein the first and second tubes are configured to be crimped onto the first and second rods, and wherein the first leg and second leg are configured to be crimped onto the screw.

Various embodiments are described, wherein the two rods have gripping features configured to engage the crimped first tube and the crimped second tube.

Various embodiments are described, the screw further includes a shank, wherein the shank has a polygonal shaped cross-section.

Various embodiments are described, further including a first crimper for crimping the first and second tubes onto the two rods and a second crimper for crimping the first and second legs onto the screw.

Various embodiments are described, further including a third rod wherein at least a first and second rod connectors are configured to slide onto the first and second rods and a third and fourth rod connectors are configured to slide onto the second and third rods.

Further various embodiments relate to a method for installing a modular crimpable bone plate system to a bone, including: screwing a plurality of screws into the bone; assembling the modular crimpable bone plate system by sliding a plurality of rod connectors onto a first rod and a second rod, wherein the rod connectors have an opening; placing the openings of the plurality of rod connectors over the heads of the plurality of screws; crimping the plurality of rod connectors to the plurality of screws; and crimping the plurality of rod connects to the first rod and the second rod.

Various embodiments are described, wherein the screw further includes a shank, wherein the shank has a polygonally shaped cross-section.

Various embodiments are described, wherein the plurality of rod connectors further include: a first tube and a second tube configured to slide over the first and second rods; and a first leg and a second leg each connected between the first and second tubes, and wherein the opening extends between the first and second legs and between the first and second tubes.

Various embodiments are described, wherein the two rods have gripping features configured to engage the crimped first tube and the crimped second tube.

Various embodiments are described, wherein crimping the plurality of rod connectors to the plurality of screws includes crimping the first and second legs to the screw.

Various embodiments are described, wherein crimping the plurality of rod connectors to the first and second rods includes crimping the first tube to the first rod and crimping the second tube to the second rod.

Various embodiments are described, wherein a first crimper crimps the first and second tubes onto the first and second rods and a second crimper crimps the first and second legs onto the screw.

Various embodiments are described, wherein screwing a plurality of screws into the bone includes screwing a first portion of the plurality of screws into a first portion of the bone on one side of a fracture in the bone and screwing a second portion of the plurality of screws into a second portion of the bone on the other side of the fracture in the bone.

Various embodiments are described, further including cutting the first and second rods to a specified length.

Further various embodiments relate to a method for installing a modular crimpable bone plate system to a bone, including: screwing a plurality of screws into the bone; assembling the modular crimpable bone plate system by sliding a first plurality of rod connectors onto a first rod and a second rod and sliding a second plurality of rod connectors onto the second rod and a third rod, wherein the rod connectors have an opening; placing the openings of the first and second plurality of rod connectors over the heads of the plurality of screws; crimping the first and second plurality of rod connectors to the plurality of screws; crimping the first plurality of rod connects to the first rod and the second rod; and crimping the second plurality of rod connects to the second rod and the third rod.

BRIEF DESCRIPTION OF THE DRAWINGS

In order to better understand various exemplary embodiments, reference is made to the accompanying drawings, wherein:

FIGS. 8A-8E describe a method of using the modular crimpable plate system;

FIGS. 13 and 14 are perspective and end views of how a three rod configuration of the modular crimpable plate system may be applied to a bone fracture.

To facilitate understanding, identical reference numerals have been used to designate elements having substantially the same or similar structure and/or substantially the same or similar function.

DETAILED DESCRIPTION

Figure 1:
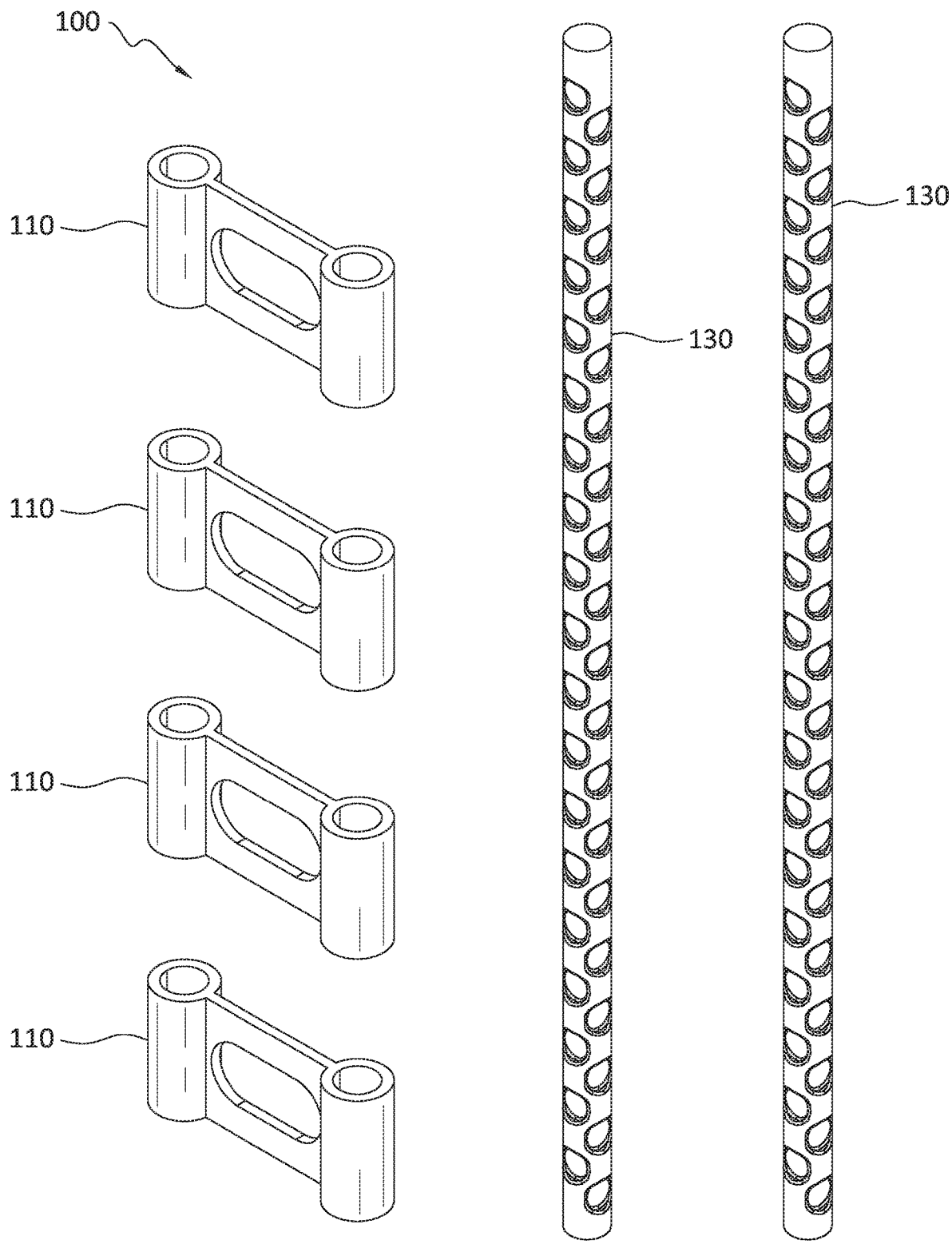
FIG. 1 illustrates the modular crimpable plate system.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Current plate and screw implant systems have limited flexibility to be used for different fracture patterns. Ideally, a surgeon should be able to place screws exactly where they are needed. Surgeons may want to capture fragments, avoid pre-existing implants, or just get screws into areas of good stable bone. Screw placement is a critical part of a successful reconstruction of the bone. Unfortunately, the plate dictates the positions of screws. Plates, particularly anatomically shaped plates, tend to fit only in one place on the bone and have a limited number of holes that the screws can pass through. Companies have developed many methods to give surgeons screw placement flexibility. Plates may have many screw holes for different patterns, have variable angle screw technology, be bendable, or come in different versions and lengths for different patterns. However, these work-arounds do not completely solve the problem. They also can be expensive and require large inventories of plates and also require the development and approval of a larger number of plates.

A modular crimpable plate system will now be described that addresses these various problems. The modular crimpable plate allows for greatly increased flexibility in screw placement. Instead of a standard plate with pre-determined holes, the modular crimpable plate system is modular and adjustable with the plate placement dictated by screw placement. The crimpable plate system comes disassembled and includes two rods (or more) and multiple rod connectors. The user first places the bone screws wherever they are needed to reconstruct the bone. The rod connectors are designed with two longitudinal tubes that accept the rods and then a central, elongated opening that will accept a bone screw. The user then slides the rod connectors onto the two rods. By aligning the rod connector openings with the head of the already-implanted screws, the user places the rod/rod connector assembly on the screws in the bone. The user then uses a crimper to deform the rod connectors around the screw heads and deform the rod connector around the rods. This creates a fixed stable structure that fixes the rods, rod connectors, and screws to one another. As the screws are securely fastened to the bone, the crimped modular crimpable plate system securely holds the bones in place.

FIG. 1 illustrates the modular crimpable plate system 100. The modular crimpable plate system 100 may include two rods 130 and a plurality of rod connectors 110. As will be described in greater detail later, the rod connectors 110 have two tubular portions that slide onto each of the two rods 130. At least two rod connectors 110 will be used.

Figure 2:
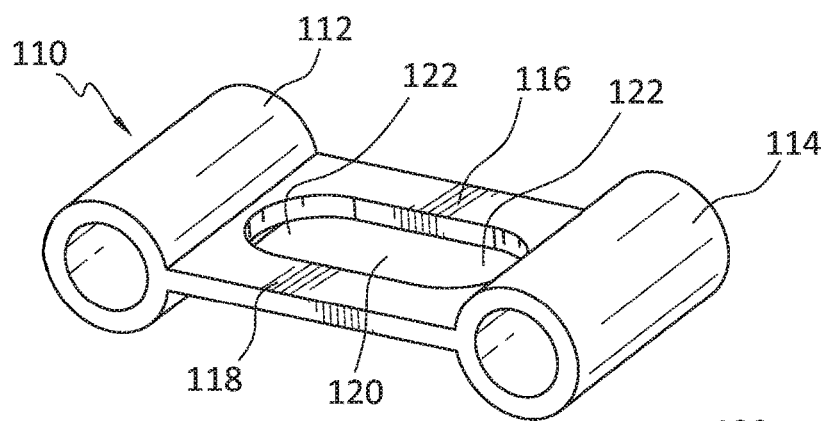
FIG. 2 illustrates an perspective view of the rod connector.
Figure 3:
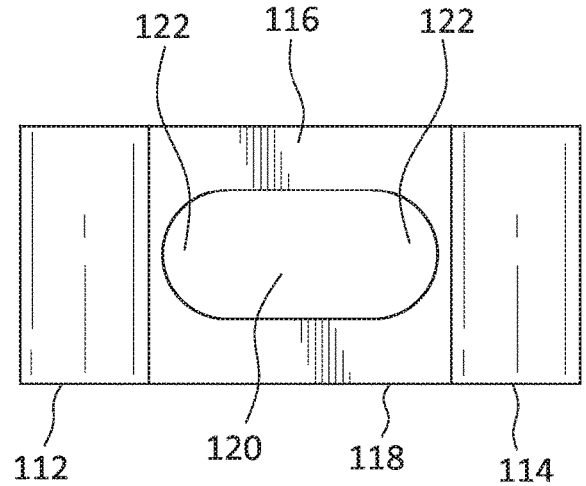
FIG. 3 shows a top view of the rod connector.

FIG. 2 illustrates a perspective view of the rod connector 110, and FIG. 3 shows a top view of the rod connector 110. The rod connector 110 includes a first tube 112 and a second tube 114 that slide over the rods 130. The first and second tubes 112, 114 are connected to one another by a first leg 116 and a second leg 118. The first and second legs 116, 118 help form an opening 120. The opening 120 is configured to accept the head of a screw. The opening 120 is shown as oval, but may be any other elongated shape including, for example, an ellipse or a rectangle. A key aspect of the opening is that is long enough to allow for the rod connector 110 to slide back and forth along a screw in the bone and over a distance sufficient to capture the screw and to affix to the screw. The opening 120 may extend completely or partially between the first and second tubes 112, 114. Further, the opening 120 is configured to be wide enough at some point along its length to fit over a screw head of the screw. In the situation where the opening 120 narrows towards its ends 122, the width of the opening 120 at the end 122 is wide enough to accommodate the shank of the screw.

The first and second tubes 112, 114 have an interior diameter sufficient to easily slide over the rods 130. The wall thickness of the tubes is selected to be thin enough so that the tubes 112, 114 may be crimped onto the rods using a crimping tool. Alternatively, the thickness and length of the tubes 112, 114 need to be large enough to provide the rigidity and strength needed to fix the bone fracture when forces are placed upon the fractured bone.

The first and second legs 116, 118 connect the first and second tubes 112, 114 and help form the opening 120. The length of the first and second legs 116, 118 may be selected to accommodate the range of potential locations of the screws in the bones. Also the width and thickness of the first and second legs 116, 118 are selected so as to allow the first and second legs 116, 118 to be crimped and to engage the shank of the screw, as well as for to provide the rigidity and strength needed to fix and stabilize the bone fracture when forces are placed upon the fractured bone.

Figure 4:
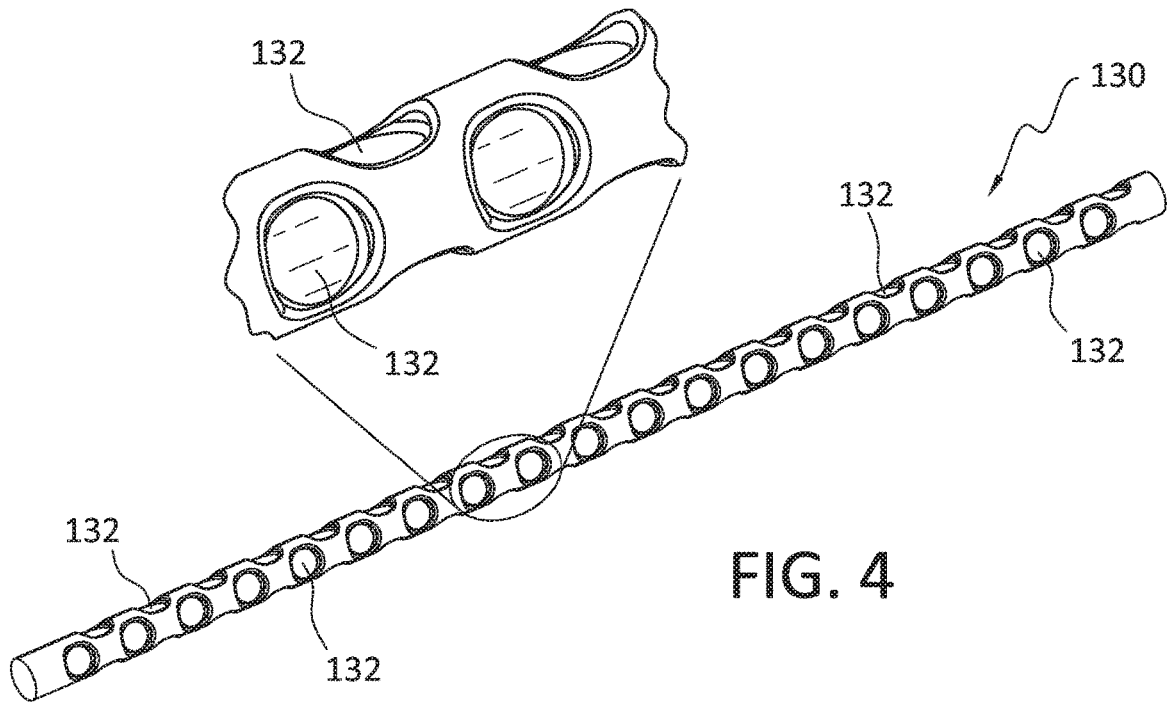
FIG. 4 illustrates an embodiment of the rod.

FIG. 4 illustrates an embodiment of the rod 130. The rod 130 is shown as having gripping features 132. The gripping features 132 may be dimples, notches, holes, grooves, etc. on the surface of the rod. The gripping features 132 are designed to provide an uneven surface so that when the tubes 112, 114 are crimped onto the rods 130, the tubes are more securely fixed to the rods 130. In FIG. 4, the griping features 132 are shown as rounded holes in the surface of the rod 130, but other shapes and types of gripping features may be used as well. The size and depth of the gripping features is selected to allow the rod connectors 110 to be securely crimped onto the rods 130, while still maintaining the strength of the rods 130. The diameter of the rods 130 is selected to provide sufficient rigidity and strength needed to fix the bone fracture when forces are placed upon the fractured bone. Further, in some situations it may be necessary to bend the rods to better conform with the bone structure to be fixed, hence the diameter of the rod 130 also need to be selected to allow for bending of the rod during surgery.

Figure 6:
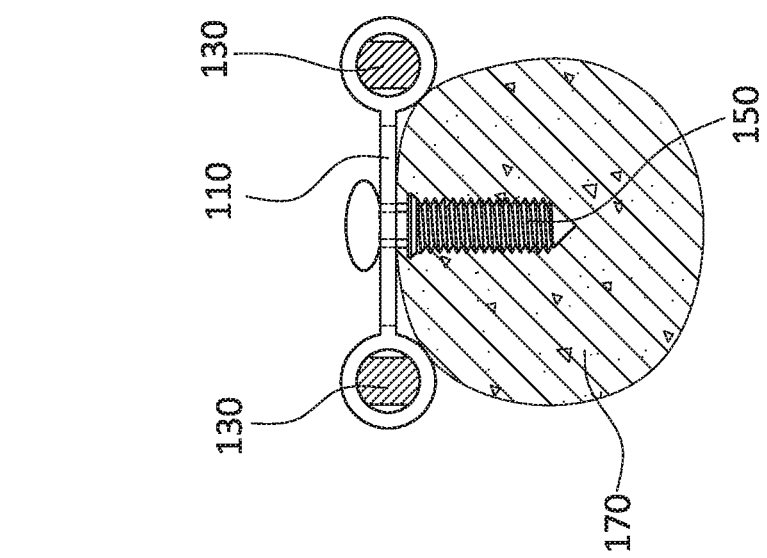
FIGS. 5 and 6 illustrate top and side views respectively of the modular crimpable plate system.
Figure 5:
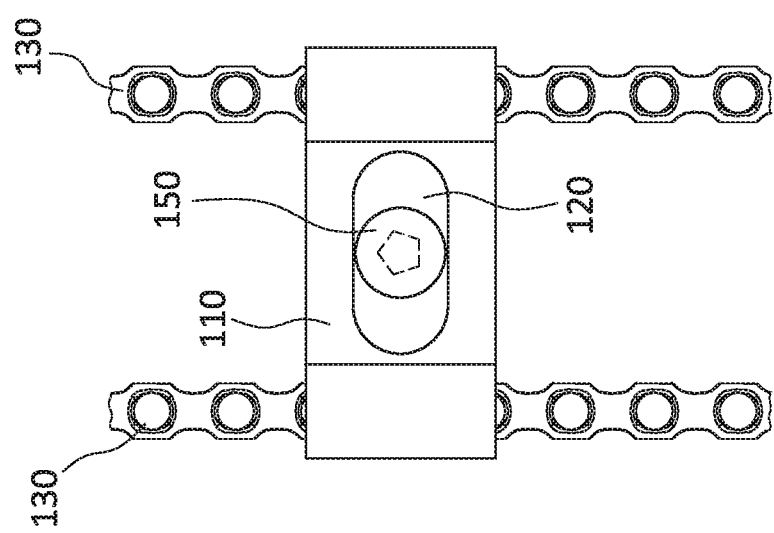

FIGS. 5 and 6 illustrate top and side views respectively of the modular crimpable plate system 100 fitted over a screw 150. The modular crimpable plate system 100 has been assembled by sliding a rod connector 120 over two rods 130. A screw 150 has been placed in the bone 170, the opening 120 of the rod connector has been placed over the screw 150, and the modular crimpable plate system 100 has been positioned to contact the bone 170.

Figure 7:
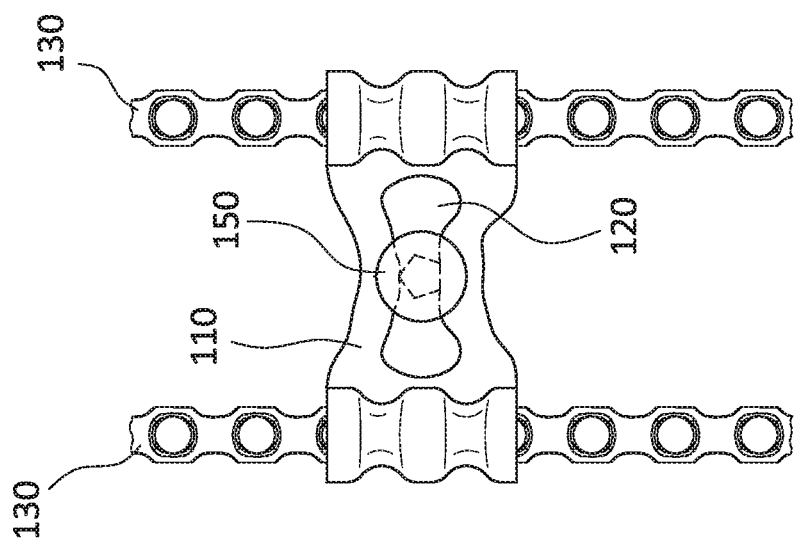
FIG. 7 illustrates a top view of the modular crimpable plate system after crimping.

With the modular crimpable plate system 100 positioned over the screws 150 in the bone, the modular plate system 100 may be crimped in place as illustrated in FIG. 7. This may be accomplished with three crimping actions. First, a first crimping tool (not shown) may be used to apply a crimping force to the outer edges of the first and second legs 112, 114 to cause them deform inward towards the screw 150, thereby collapsing the opening 120 so that the crimped first and second legs 112, 114 securely engage the screw to thereby securely fix the rod connector to the screw 150. The first crimping tool may be any tool that provides sufficient crimping force to deform the first and second legs 112, 114. Such a tool may be a hand tool that provides sufficient mechanical advantage so that a user may operate the crimper by hand. In other situations, the first crimping tool may be a powered tool.

The second and third crimping actions may be on the first and second tubes 116, 118, where a second crimping tool is used to crimp the first and second tubes 116, 118 onto the rods 130. The second crimping tool applies sufficient force on the first and second tubes 116, 118 to cause them to collapse to thereby securely fix the rod connector to the rods 130. The second crimping tool may be any tool that provides sufficient crimping force to deform the first and second tubes 116, 118. For example, the second crimping tool may apply a force on a top and bottom side of the first and second tubes 116, 118 so as to cause the tube to deform and engage the rods 130. Other crimping configurations may be used as well. Such a tool may be a hand tool that provides sufficient mechanical advantage so that a user may operate the crimper by hand. In other situations, the first crimping tool may be a powered tool.

FIGS. 8A-8E describe a method of using the modular crimpable plate system 100. The first step of placing screws in the bone 170 is illustrated in FIG. 8A. In this case the surgeon has placed 6 screws 150 in the fractured bone 170—three on each side of the fracture. The screws are placed by the surgeon in the best locations, based upon various factors and to provide the most secure fixation of the bone. For example, in some fractures their may be more than two bone fragments that need to be captures by screws. Further, it is noted that the distance between the screws is limited by the length of the rod connectors 110 so that adjacent rod connectors 110 do not interfere with one another. In the next step, modular crimpable plate system 100 is assembled using two rods 103 and 6 rod connectors 110 as illustrated in FIG. 8B. The number of rod connectors is selected to match the number of screws placed by the surgeon in the first step. Accordingly, fewer or more rod connectors and screws may be used with the modular crimpable plate system 100. The rod connectors 110 may be positioned on the rods 130 to roughly correspond to the positions of the screws 150 in the bone 170. Also, the rods 130 may be cut to the desired length based upon the specific application and location of the modular crimpable plate system 100. In the third step, the surgeon takes modular crimpable plate system 100 and slides the rod connectors 110 over the heads of the screws 150 as illustrated in FIG. 8C. This may be easily done because the rod connectors 110 may slide along the rods 130 to the correct position of each screw 150 along the bone 170. Further, the length of the openings 120 in the rod connectors 110 is sufficient to accommodate the lateral variation in the location of the screws 150 in the bone 170. In step four, the rod connectors 110 are crimped to the screws 150 as described above to fix the rod connectors 110 to their respective screws 150 as illustrated in FIG. 8D. In step five, the rod connectors 110 are crimped to the rods 130 as described above to fix the rod connectors 110 to the two rods 130 as illustrated I FIG. 8E.

Figure 9:
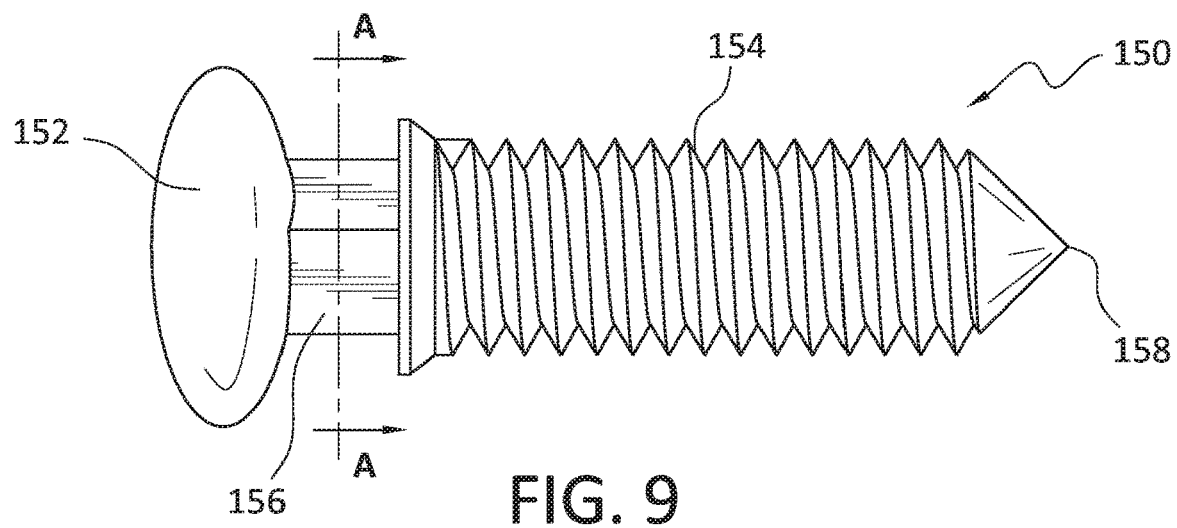
FIG. 9 illustrates an embodiment of a screw.
Figure 10:
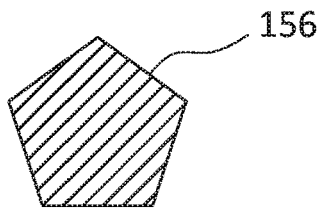
FIG. 10 illustrates a cross-section of the shank of the screw.
Figure 11:
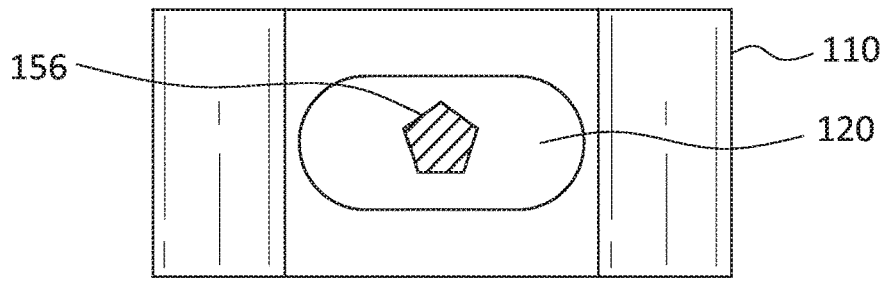
FIG. 11 illustrates the cross-section of the shank as it sits inside the opening of the rod connector.
Figure 12:
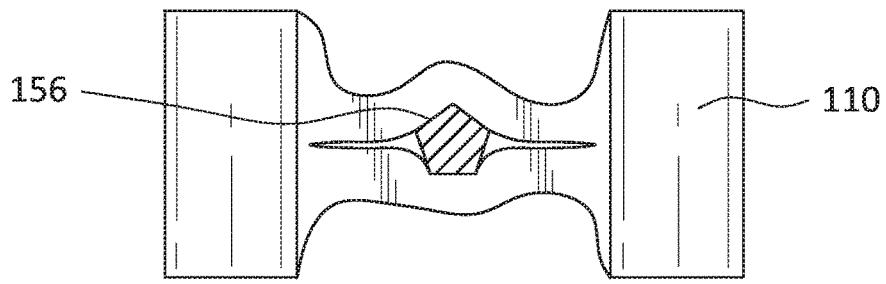
FIG. 12 illustrates the cross-section of the shank inside the opening after crimping.

FIG. 9 illustrates an embodiment of a screw 150. The screw 150 includes a screw head 152, a threaded portions 154, a shank 156, and tip 158. In this embodiment of the screw the shank 156 is shown as having pentagonal cross-section (see FIG. 10). The shank 156 is the portion of the screw 150 that engages with the crimped first and second legs 112, 114. The pentagonal shape of the shank helps facilitate a more secure fixation of the rod connector 110 on the screw 150. FIG. 11 illustrates the cross-section of the shank 156 as it sits inside the opening 120 of the rod connector 110. FIG. 12 illustrates the cross-section of the shank 156 inside the opening 120 after crimping. As can be seen in FIG. 12, the pentagonal shape allows for the crimped rod connector 110 to be more securely fixed to the screw 130 and helps to prevent rotation of the crimped rod connector 110 about the screw 150. For example, if the shank is round the crimped rod connector 110 could rotate around the shank of the screw, unless significant crimping force is applied to the rod connector 110. The shank may also have other cross-sections such as a triangle, square, rectangle, hexagon, other polygonal shapes, etc.

The rod connector 110, the rod 130, and the screw 150 each may be made of a medical grade material that may be implanted in a living body. Such materials may include titanium or medical grade stainless steel of various varieties. The material along with dimensions of the rod connector 110 are selected so as to allow for the crimping of the rod connector 110 to the rods 130 and the screws 150, as well as providing sufficient rigidity and strength after being crimped to secure the fractured bone. Also the length of the rod connector affects how closely screw may be placed in the bone. Further, the material and dimensions of the rods 130 are selected so as to allow for the bending and cutting of the rods 130 as needed for specific applications, as well providing sufficient rigidity and strength to secure the fractured bone.

In the example provided in FIG. 8, two rods were used along with 6 rod connectors 110. More or fewer rod connectors may be used based upon the specific application of the modular crimpable plate system 100.

In yet another embodiment three rods may be used. FIGS. 13 and 14 are perspective and end views of how a three rod configuration of the modular crimpable plate system 100 may be applied to a bone fracture. For example, if it were beneficial or required to place screws in the bones having a large difference in radial position about the circumference of the bone (e.g., if the screws ended up with and angle between them of about 20° to 90°), the three rods could be used to create a roughly L-shaped configuration. In the example shown in FIGS. 13 and 14, four screws are placed in the bone, with two screws on each side of the fracture 172. Because of the large radial angular difference between the two screws 150 on each side of the fracture 172, a two rod solution cannot be used with this screw placement. Instead first and second rods 130a and 130b are used with first and second rod connectors 110a and 110b. This structure may engage screws 150a and 150b. The second and third rods 130b and 130c are used with third and fourth rod connectors 110c and 110d to engage screws 150c and 150d. In this application of three rods, the location of the screws is selected so that rod connectors do not interfere with one another like in the two rod situation. If need be, this solution could be extended to 4 or more rods as well. Any number of rod connectors may be used based upon the number of screws needed to secure the bone fracture.

The modular crimpable plate system 100 may come in a sterilized kit. Such a kit could include a specific number of rods, rod connectors, and screws. The kit could also include crimping tools, but such tools may also be separate from the kit. Further, kits with elements having different sizes may be available in order to have kits for use in different applications around the body that require different sized plates.

The modular crimpable plate system allows for easy adjustment of the rod connectors on the rods allowing the screws to be placed anywhere along the bone that is desirable and beneficial. Because of the adjustability, a single kit may be used in a wide variety of applications. This decreases the number of different types of inventory items needed to treat bone fractures. The rods in the kits may be sized to be long enough to cover many applications, and the rod may then be cut to size during the surgery.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A modular crimpable bone plate system, comprising:
a first rod and a second rod; and
a plurality of rod connectors, wherein the rod connectors further comprise:
   a first tube and a second tube configured to slide over the first and second rods;
   a first leg and a second leg each connected between the first and second tubes; and
   an opening between the first and second legs and between the first and second tubes, wherein the opening is configured to accept a screw head of a screw;
wherein the first and second tubes are configured to be crimped onto the first and second rods, and wherein the first leg and the second leg are configured to be crimped onto the screw.

2. The system of claim 1, wherein the first and second rods have gripping features configured to engage the crimped first tube and the crimped second tube.

3. The system of claim 1, wherein the screw further includes a shank, wherein the shank has a polygonal shaped cross-section.

4. The system of claim 1, further comprising a first crimper for crimping the first and second tubes onto the first and second rods and a second crimper for crimping the first and second legs onto the screw.

5. The system of claim 1, further comprising a third rod wherein at least a first and second rod connectors are configured to slide onto the first and second rods and a third and fourth rod connectors are configured to slide onto the second and third rods.

6. A method for installing a modular crimpable bone plate system to a bone, comprising:
screwing a plurality of screws into the bone;
assembling the modular crimpable bone plate system by sliding a plurality of rod connectors onto a first rod and a second rod, wherein the rod connectors have an opening;
placing the openings of the plurality of rod connectors over heads of the plurality of screws;
crimping the plurality of rod connectors to the plurality of screws; and
crimping the plurality of rod connectors to the first rod and the second rod.

7. The method of claim 6, wherein the screw further includes a shank, wherein the shank has a polygonally shaped cross-section.

8. The method of claim 6, wherein the plurality of rod connectors further comprise:
a first tube and a second tube configured to slide over the first and second rods; and
a first leg and a second leg each connected between the first and second tubes, and
wherein the opening extends between the first and second legs and between the first and second tubes.

9. The method of claim 8, wherein the first and second rods have gripping features configured to engage the crimped first tube and the crimped second tube.

10. The method of claim 8, wherein crimping the plurality of rod connectors to the plurality of screws includes crimping the first and second legs to the screw.

11. The method of claim 8, wherein crimping the plurality of rod connectors to the first and second rods includes crimping the first tube to the first rod and crimping the second tube to the second rod.

12. The method of claim 8, wherein a first crimper crimps the first and second tubes onto the first and second rods and a second crimper crimps the first and second legs onto the screw.

13. The method of claim 6, wherein screwing a plurality of screws into the bone includes screwing a first portion of the plurality of screws into a first portion of the bone on one side of a fracture in the bone and screwing a second portion of the plurality of screws into a second portion of the bone on the other side of the fracture in the bone.

14. The method of claim 6, further comprising cutting the first and second rods to a specified length.

15. A method for installing a modular crimpable bone plate system to a bone, comprising:
screwing a plurality of screws into the bone;

assembling the modular crimpable bone plate system by sliding a first plurality of rod connectors onto a first rod and a second rod and sliding a second plurality of rod connectors onto the second rod and a third rod, wherein the rod connectors have an opening;

placing the openings of the first and second plurality of rod connectors over heads of the plurality of screws;

crimping the first and second plurality of rod connectors to the plurality of screws;

crimping the first plurality of rod connectors to the first rod and the second rod; and crimping the second plurality of rod connectors to the second rod and the third rod.

16. The method of claim 15, wherein the screw further includes a shank, wherein the shank has a polygonally shaped cross-section.

17. The method of claim 15, wherein the plurality of rod connectors further comprise:

a first tube and a second tube configured to slide over the first and second rods; and a first leg and a second leg each connected between the first and second tubes, and wherein the opening extends between the first and second legs and between the first and second tubes.

18. The method of claim 15, wherein the first and second rods have gripping features configured to engage the crimped first tube and the crimped second tube.

19. The method of claim 15, wherein crimping the plurality of rod connectors to the plurality of screws includes crimping the first and second legs to the screw.

20. The method of claim 15, wherein crimping the first plurality of rod connectors to the first and second rods includes crimping the first tube to the first rod and crimping the second tube to the second rod.

\* \* \* \* \*